United States Patent [19]

Ohst et al.

[11] Patent Number: 5,036,151

[45] Date of Patent: Jul. 30, 1991

[54] MOLD RELEASEL AGENTS FOR POLY(ESTER) CARBONATES

[75] Inventors: Holger Ohst, Bergisch Gladbach; Helmut-Martin Meier, Ratingen; Klaus Kircher, Leverkusen, all of Fed. Rep. of Germany

[73] Assignee: Bayer Aktiengesellschaft, Leverkusen, Fed. Rep. of Germany

[21] Appl. No.: 493,269

[22] Filed: Mar. 14, 1990

[30] Foreign Application Priority Data

Mar. 16, 1989 [DE] Fed. Rep. of Germany ....... 3908598

[51] Int. Cl.$^5$ .................. C08K 5/3492; C07D 251/32; C09K 15/32
[52] U.S. Cl. .................................... 524/101; 544/193; 544/221; 252/400.24
[58] Field of Search ................ 524/101; 544/193, 221; 252/400.24

[56] References Cited

U.S. PATENT DOCUMENTS

| | | | |
|---|---|---|---|
| 4,243,570 | 1/1981 | Mark et al. | 260/30.2 |
| 4,582,888 | 4/1986 | Kase et al. | 544/193 |
| 4,627,949 | 12/1986 | Dhein et al. | 264/101 |
| 4,837,321 | 6/1989 | Kerimis et al. | 544/193 |

FOREIGN PATENT DOCUMENTS 1166316 10/1969 United Kingdom .

Primary Examiner—Kriellion S. Morgan
Attorney, Agent, or Firm—Joseph C. Gil; Thomas W. Roy

[57] ABSTRACT

The invention relates to trimerized aliphatic isocyanates produced by special processes, to their use as mold release agents in thermoplastic aromatic polycarbonates and/or thermoplastic aromatic polyestercarbonates and/or thermoplastic aromatic polyesters, optionally using standard additives, to the readily demoldable molding compounds thus obtained on the basis of the thermoplastic polycarbonates, polyestercarbonates and/or polyesters and to processes for the production of these readily demoldable molding compounds.

10 Claims, No Drawings

MOLD RELEASEL AGENTS FOR POLY(ESTER) CARBONATES

It is known that various catalysts may be used for the trimerization of alkyl isocyanates, including for example lithium oxide, sodium methoxide, sodium formate, sodium carbonate, sodium benzoate, sodium borohydride, potassium tert.-butylate, alkali soaps, lead salts, titanium tetrabutylate, triethylamine, oxalic acid, organic compounds of tetravalent tin and also triethyl phosphane (H. Ulrich, Cycloaddition Reactions of Heterocumulenes, 1967, pages 128 et seq, Academic Press).

Trialkyl phosphanes and aryl alkyl phosphanes and also organometallic compounds of elements of groups IVa, IVb, Va and IIb of the PSE have also been described as catalysts (S. Patai, The Chemistry of Cyanates and Thio-Derivatives, 1977, pages 674 et seq).

Trialkyl phosphanes are also mentioned as catalysts in Kirk-Othmer, Encyclopedia of Chemical Technology, Vol. 13, page 794, 1981.

Long-chain aliphatic isocyanurates are known and have been used as additives for elastomers (EP 136 898), as foam inhibitors (DOS 1 965 643), as waterproofing agents (C.A. No. 55, 24564 c) and as insecticides (C.A. No. 104, 16499 n). Trialkyl isocyanurates have also been mentioned as flow promoters for high molecular weight aromatic polycarbonates and polyester carbonates (U.S. Pat. No. 4,243,570).

Numerous compounds have been described as mold release agents for polycarbonate, including for example fatty acids (EP 189 572), ketones (EP 100 918), vinyl ethers (U.S. Pat. No. 4,438,234), N,N-diallylamides (U.S. Pat. No. 4,554,302), siloxanes (U.S. Pat. No. 3,751,519), paraffins and alkanes (U.S. Pat. No. 4,415,696, U.S. Pat. No. 4,626,566), perfluoroalkyl sulfonamides (DOS 2 506 726) and, in particular, fatty acid esters (EP 103 107, DOS 2 729 485, U.S. Pat. No. 4,131,575, U.S. Pat. No. 4,097,435, U.S. Pat. No. 3,836,499).

Insofar as each class of compounds in the patents cited above may be useful as mold release agents for polycarbonates, particular reference is made to those patents. Besides their effectiveness as mold release agents, each of the above-mentioned classes of compounds in polycarbonate meet the particular additional demands made of them in individual aspects insofar as they are transparent, show little discoloration and undergo minimal degradation in molecular weight under thermal stressing. However, where these additional requirements have to be satisfied simultaneously in all the aspects mentioned, the classes of compounds mentioned above are unsuitable as mold release agents.

It has been found that, considering all the requirements which a modern polycarbonate molding material has to satisfy, the classes of compounds mentioned above are all attended by disadvantages either by affecting transparency (for example siloxanes, paraffins and alkanes) or by promoting molecular weight degradation of the polycarbonate/polyestercarbonate. Fatty acid esters in particular adversely affect long-term thermal behavior by transesterification and, hence, degradation at high temperatures. Despite the number of mold release agents described in patent specifications, there is still a need in practice for a component which does not adversely affect color or transparency, which has no significant effect on short-term mechanical, electrical and thermal properties and which, despite very good behavior as a mold release agent, does not significantly affect long-term thermal behavior.

Surprisingly, a long-chain aliphatic isocyanurate prepared from corresponding isocyanates using triaryl phosphane as catalyst has proved to be a highly effective mold release agent in polycarbonate and/or aromatic polyestercarbonates and/or aromatic polyesters without showing any of the disadvantages mentioned above.

Aliphatic isocyanurates produced in accordance with the prior art present problems when used in polycarbonate. Both acidic catalysts (for example organotin compounds) and also basic catalysts (for example sodium methoxide, triethyl phosphane) cause serious molecular weight degradation in polycarbonates. The quantitative removal of these catalysts from the isocyanurate formed is problematical (distillation, crystallization or neutralization). Trimerization without a catalyst is not possible.

Surprisingly, the trimerization of aliphatic isocyanates is possible using triaryl phosphanes, particularly triphenyl phosphane, as catalyst.

Accordingly, the present invention relates to a process for the trimerization of aliphatic isocyanates at temperatures in the range from 50° to 250° C. and preferably at temperatures in the range from 150° to 220° C. and under pressures of 0.1 bar to 100 bar and preferably under pressures of 1 bar to 10 bar either in air or an inert gas in the presence of catalysts, characterized in that triaryl phosphanes are used in quantities of 0.1% by weight to 10% by weight and preferably in quantities of 1% by weight to 5% by weight, based on the aliphatic isocyanate used, and the reaction is continued to an NCO value of 0%. (For NCO value, see Vieweg-Höchtlen, Kunststoff-Handbuch, Vol. VII, 1966, page 90). Nitrogen for example is used as the inert gas.

The present invention also relates to the isocyanurates obtainable by the process according to the invention.

The invention also relates to the use of the isocyanurates obtainable in accordance with the invention as mold release agents for thermoplastic aromatic polycarbonates, for thermoplastic aromatic polyestercarbonates and for thermoplastic aromatic polyesters.

The present invention also relates to mixtures of thermoplastic aromatic polycarbonates and/or mixtures of thermoplastic aromatic polyestercarbonates and/or mixtures of thermoplastic aromatic polyesters with the isocyanurates obtainable in accordance with the invention in quantities of from 0.05% by weight to 3% by weight and preferably in quantities of from 0.1% by weight to 1% by weight, based on the weight of the polycarbonate and/or the polyestercarbonate and/or the polyester.

As already mentioned, the catalyst, i.e. the triaryl phosphane, is not removed from the trimerized isocyanurate, so that it is incorporated in the polycarbonates and in the polyestercarbonates and in the polyesters where the isocyanurate is used as a mold release agent. However, the triaryl phosphane may also be used in larger quantities, based on the mixture of mold release agents, of up to at most about 65% by weight, based on the total weight of isocyanurate + triaryl phosphane.

Accordingly, the present invention also relates to mixtures of trimerized aliphatic isocyanate and triaryl phosphane, the trimerized aliphatic isocyanate being used in quantities of 99.9% by weight to 35% by weight and the triaryl phosphane in quantities of 0.1% by weight to 65% by weight, based on the total weight of isocyanurate and triaryl phosphane.

The present invention also relates to the use of the mixture of trimerized aliphatic isocyanate and triaryl phosphane according to the invention as a mold release agent for polycarbonates and for polyestercarbonates and for polyesters and for mixtures of polycarbonates and/or polyestercarbonates and/or polyesters.

Where this mixture is used, the total weight of isocyanurate and triaryl phosphane in the polycarbonate or in the polyestercarbonate or in the polyester is from 0.05 to 3% by weight and preferably from 0.1 to 1% by weight, as mentioned above.

The present invention also relates to mixtures of thermoplastic aromatic polycarbonates and/or mixtures of thermoplastic aromatic polyesterpolycarbonates and/or mixtures of thermoplastic aromatic polyesters with the trimerized aliphatic isocyanates and with triaryl phosphanes, the content of the mixture of trimerized aliphatic isocyanate and triaryl phosphane according to the invention again being from 0.05% by weight to 3% by weight and preferably from 0.1% by weight to 1% by weight, based on the weight of the polycarbonate and/or the polyestercarbonate and/or the polyester.

As already mentioned, it is known from U.S. Pat. No. 4,243,570 that isocyanurates, including trialkyl isocyanurates for example, may be used as flow promoters for polycarbonates and polyestercarbonates. The production of the isocyanurates is not specified in this US patent which merely states that the isocyanurates may be produced by conventional methods as described, for example, in Kirk-Othmer, Encyclopedia of Chemical Technology, Vol. 20, pages 662 to 671, John Wiley & Sons, 1969, New York (column 2, lines 3 to 8 of U.S. Pat. No. 4,243,570).

Triaryl phosphane is known as a stabilizer for polycarbonate from EP-P 0 143 906 and the literature cited therein.

In applicants' view, the use of mixtures of aliphatic isocyanurates with triaryl phosphanes as mold release agents is not obvious from these two literature references, especially since mold release and flow promotion rarely involve identical processes.

It is known that the flow of polycarbonates can be improved by the addition of small amounts of polyalkylene terephthalates and/or organic phosphoric acid esters. However, the improvement in flow obtainable in this way is not accompanied by any significant improvement in demolding behavior. On the other hand, the esters of long-chain organic acids and alcohols known as effective mold release agents do not act significantly as flow promoters. An improvement in flow is only obtained with conventional mold release agents in cases where alkaline or aminic impurities damage the polymer molecule during processing and lead to a reduction in molecular weight which is undesirable in practice.

Suitable aliphatic isocyanates are both aliphatic isocyanates in the narrower sense, i.e. those containing alkyl radicals, and also cycloliphatic isocyanates, i.e. those containing cycloalkyl radicals.

In the context of the invention, isocyanates are understood to be both monoisocyanates and also diisocyanates. Accordingly, the isocyanates in question are referred to collectively as (cyclo)aliphatic (mono- and di-)isocyanates.

Preferred (cyclo)aliphatic monoisocyanates are those corresponding to formula (I)

$$R-N=C=O \tag{1}$$

in which R is a $C_{1-30}$ alkyl radical or a $C_{4-12}$ cycloalkyl radical, $C_{12-24}$ alkyl radicals being particularly preferred.

Preferred (cyclo)aliphatic diisocyanates are those corresponding to formula (2)

$$OCN-R'-NCO \tag{2}$$

in which R' is a $C_{2-14}$ alkylene or a $C_{4-12}$ cycloalkylene, $C_{6-10}$ alkylenes and $C_{6-10}$ cycloalkylenes being particularly preferred.

The (cyclo)aliphatic diisocyanates are only used in conjunction with the (cyclo)aliphatic monoisocyanates in quantities of up to 10% by weight and preferably in quantities of up to 2% by weight, based on the weight of the particular monoisocyanate used.

Triaryl phosphanes suitable for use in accordance with the invention are those containing $C_{6-14}$ aryl radicals which may optionally be substituted once or several times by alkyl, aryl or halogen substituents.

Preferred triaryl phosphanes are those corresponding to formula (3)

$$\begin{array}{c} R''-P-R''' \\ | \\ R^{IV} \end{array} \tag{3}$$

in which R", R''', and $R^{IV}$ represent phenyl or naphthyl which may be substituted once or several times by $CH_3$, $C_2H_5$, $C_6H_5$, F, Cl or Br.

Examples of monoisocyanates are ethyl isocyanate, propyl isocyanate, butyl isocyanate, isopropyl isocyanate, sec.-butyl isocyanate, isobutyl isocyanate, tert.-butyl isocyanate, dodecyl isocyanate, hexadecyl isocyanate, stearyl isocyanate, cyclohexyl isocyanate, 3,3,5-trimethyl cyclohexyl isocyanate, 2-norbornyl methyl isocyanate.

Preferred monoisocyanates are, for example, dodecyl isocyanate, hexadecyl isocyanate, stearyl isocyanate and mixtures of these isocyanates.

Examples of diisocyanates are hexamethylene diisocyanate, 2,2,4-trimethyl-1,6-diisocyanatohexane, 1,4-diisocyanatocyclohexane, 3,3,5-trimethyl-1-isocyanato-3-isocyanatomethyl cyclohexane, dimeryl diisocyanates, bis-(4-isocyanatocyclohexyl)-methane.

The preferred diisocyanate is, for example, hexamethylene diisocyanate.

Suitable triaryl phosphanes are, for example, triphenyl phosphane, tris-p-tolyl phosphane, tris-(p-nonylphenyl)-phosphane, tris-naphthyl phosphane, tris-(p-chlorophenyl)-phosphane, tris-(p-fluorophenyl)-phosphane and mesityl phenyl-o-chlorophenyl phosphane.

Triphenyl phosphane is particularly preferred.

Both the isocyanates and the triaryl phosphanes may be used individually and in the form of mixtures of two different isocyanates and two different triaryl phosphanes, with the proviso that the sum of the particular diisocyanates used amounts to at most 10% by weight of the sum of the particular monoisocyanates used.

The resulting trimerized isocyanates preferably have the structural formula (4a)

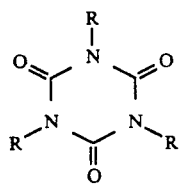

or the structural formula (4b)

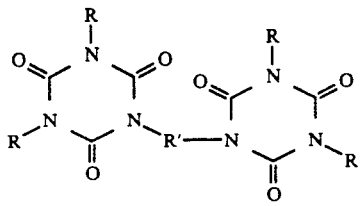

or oligomeric structures with more than two isocyanurate rings, i.e. those containing at least one structural unit (4c)

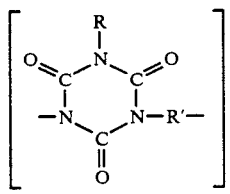

and, in the case of branches, at least one structural unit (4d)

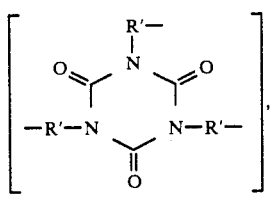

in which R and R' are as defined for formulae (1) and (2). Mixtures of the structures (4a) with (4b) and/or with those based on (4c) and/or (4d) may optionally be present.

The trimerized isocyanates obtainable by the process according to the invention accumulate in the form of glass-like solidified melts which can be reduced to powder.

Where the mixtures according to the invention of the trimerized aliphatic isocyanates and the triaryl phosphanes are to be produced by methods other than the trimerization of the aliphatic isocyanates in the presence of triaryl phosphanes in accordance with the invention, the following procedure for example is best adopted:

Trisubstituted isocyanurates may generally be obtained by alkylation of isocyanuric acid. For example, the alkylation of isocyanuric acid with n-hexyl chloride at elevated temperature in a yield of 71% is described in Kirk Othmer, Encyclopedia of Chemical Technology, Vol. 7, page 401, 1979. These trialkylated isocyanurates may then be mixed in the desired quantities with the triaryl phosphanes in known manner to form the mold release agents according to the invention.

Thermoplastic aromatic polycarbonates in the context of the invention are the polycondensates obtainable by reaction of diphenols, particularly dihydroxydiaryl alkanes, with phosgene or diesters of carbonic acid, dihydroxydiaryl alkanes in which the aryl radicals bear methyl groups or halogen atoms in the o- and/or m-position to the hydroxyl group also being suitable in addition to the unsubstituted dihydroxydiaryl alkanes. Branched polycarbonates are also suitable. Monophenols for example are used as chain terminators and trisphenols or tetraphenols for example as branching agents.

The polyester carbonates have average weight average molecular weights $\overline{M}w$ in the range from 10,000 to 300,000 and preferably in the range from 50,000 to 250,000 on the one hand and from 20,000 to 40,000 on the other hand, as determined by gel permeation chromatography or by measurement of the relative viscosity in $CH_2Cl_2$ at 25° C. and at a concentration of 0.5 g per 100 ml.

Suitable diphenols are, for example, hydroquinone, resorcinol, 4,4'-dihydroxydiphenyl, bis-(hydroxyphenyl)-alkanes, such as for example $C_{1-8}$ alkylene or $C_{2-8}$ alkylidene bisphenols, bis-(hydroxyphenyl)-cycloalkanes, such as for example optionally substituted $C_{5-15}$ cycloalkylene or optionally substituted $C_{5-15}$ cycloalkylidene bisphenols, bis-hydroxyphenyl)-sulfides, ethers, ketones, sulfoxides or sulfones, also $\alpha,\alpha'$-bis-(hydroxyphenyl)-diisopropylbenzene and the corresponding nucleus-alkylated and nucleus-halogenated compounds.

Preferred polycarbonates are those based on bis-(4-hydroxyphenyl)-2,2-propane (bisphenol A), bis-(4-hydroxy-3,5-dichlorophenyl)-2,2-propane (tetrachlorobisphenol A), bis-(4-hydroxy-3,5-dibromophenyl)-2,2-propane (tetrabromobisphenol A), bis-(4-hydroxy-3,5-dimethylphenyl)-2,2-propane (tetramethyl bisphenol A), bis-(4-hydroxyphenyl)-1,1-cyclohexane (bisphenol Z), 1,1-bis-(4-hydroxyphenyl)-3,3,5-trimethyl cylohexane (TMC bisphenol) according to German patent application P 38 32 396.6 (LE A 26 344) and those based on trinuclear bisphenols, such as $\alpha,\alpha'$-bis-(4-hydroxyphenyl)-p-diisopropylbenzene. Other suitable diphenols and the production of the polycarbonates are described, for example, in U.S. Pat. Nos. 3,028,365, 3,062,781 and 3,879,347.

Branched polycarbonates are described, for example, in U.S. Pat. No. 4,185,009 and in DE-PS 2 500 092.

Thermoplastic aromatic polyesters in the context of the present invention are those based on diphenols, aromatic dicarboxylic acid dichlorides, chain terminators and, optionally, branching agents.

Suitable diphenols are the compounds mentioned above for the production of the polycarbonates.

Monophenols are used as chain terminators and trisphenols and tetraphenols as branching agents.

In addition, aromatic tricarboxylic acid trichlorides or aromatic tetracarboxylic acid tetrachlorides or acid chlorides of even higher aromatic carboxylic acids may also be used with advantage as branching agents.

They are used in quantities of from 0.01 to 1 mol-%, based on the aromatic dicarboxylic acid dichlorides used, whereas where phenolic branching agents are used the quantity of 0.01 to 1 mol-% is based on the diphenols used for the production of the aromatic polyester.

Branching agents for the production of aromatic polyesters are described, for example, in DE-OS 2 940 024, pages 9/10 (LE A 19 932).

Suitable aromatic dicarboxylic acid dichlorides are terephthalic acid dichloride, isophthalic acid dichloride, o-phthalic acid dichloride, diphenyl dicarboxylic acid dichloride, diphenyl ether dicarboxylic acid dichloride, naphthalene dicarboxylic acid dichloride and mixtures thereof.

Preferred mixtures are mixtures of terephthalic acid dichlorides with isophthalic acid dichlorides in a ratio of 20:1 to 1:20 and more especially in a ratio of 7:3 to 3:7.

The production of the aromatic polyesters from acid dichlorides, diphenols, chain terminators and, optionally, branching agents is preferably carried out in known manner by the interfacial polycondensation process (cf. for example DE-OS 2 940 024 and for the TMC-Bisphenol German Patent Application P 3903103.9 ( Le A 26 313)).

Thermoplastic aromatic polyestercarbonates in the context of the invention are those obtainable in known manner from diphenols, phosgene, aromatic dicarboxylic acid dichlorides, chain terminators and, optionally, branching agents. Polyestercarbonates and their production are known (cf. for example EP-OS 0 036 080 (Le A 20 203) and U.S. Pat. No. 3,169,121 and for the TMC-Bisphenol German Patent Application P 3903103.9 ( Le A 26 313)).

Suitable diphenols are those mentioned above for the production of polycarbonates.

Suitable aromatic dicarboxylic acid dichlorides are those already mentioned for the production of aromatic polyesters, mixtures of terephthalic acid dichlorides with isophthalic acid dichlorides in the ratios already mentioned being particularly suitable.

Suitable chain terminators are the monophenols already mentioned as suitable for the production of polycarbonates and polyesters.

Suitable branching agents are the more than dihydric phenols and more than difunctional aromatic carboxylic acid chlorides mentioned above for the aromatic polyesters.

The aromatic polyestercarbonates according to the invention contain up to about 80 mol-% and preferably up to about 50 mol-% carbonate groups, based on the mol total of carbonate groups and aromatic carboxylic acid ester groups.

Both the ester component and the carbonate component of the aromatic polyestercarbonates according to the invention may be present in the polycondensate in the form of blocks or in statistical distribution.

The relative solution viscosity ($\eta_{rel}$) of the aromatic polyesters and polyester carbonates is in the range from 1.18 to 1.4 and preferably in the range from 1.22 to 1.3 (as measured on solutions of 0.5 g polyester respectively polyestercarbonate in 100 ml $CH_2Cl_2$ solution at 25° C.).

The trimerized isocyanates obtainable in accordance with the invention or the mixtures according to the invention of the separately prepared isocyanurates and the triaryl phosphanes may be incorporated in the thermoplastic aromatic polycarbonates and/or the thermoplastic aromatic polyestercarbonates and/or the thermoplastic aromatic polyesters, for example, by rolling onto the plastic granulate, subsequent homogenization in an extruder and regranulation. However, they may also be incorporated during the actual production of the polycarbonates and/or the polyestercarbonates and/or the polyesters.

Other additives typical of polycarbonates, polyestercarbonates or polyesters, for example impact modifiers, stabilizers, flameproofing agents, pigments and also fillers and reinforcing materials, may be incorporated in the molding compounds according to the invention in the usual quantities before or during or after incorporation of the mold release agents according to the invention.

The present invention also relates to mixtures of thermoplastic, aromatic polycarbonates and/or mixtures of thermoplastic aromatic polyestercarbonates and/or mixtures of thermoplastic aromatic polyesters with the mold release agents to be used in accordance with the invention and with at least one standard additive selected from impact modifiers, stabilizers, flameproofing agents, pigments, fillers and reinforcing materials in the usual quantities.

Accordingly, the present invention also relates to a process for the production of thermoplastic molding compounds of thermoplastic aromatic polycarbonates and/or thermoplastic aromatic polyestercarbonates and/or thermoplastic aromatic polyesters, characterized in that the mold release agents obtainable in accordance with the invention, i.e. the isocyanates trimerized in accordance with the invention or the mixtures according to the invention of isocyanurates and triaryl phosphanes are added to thermoplastic polycarbonate and/or thermoplastic polyestercarbonate and/or thermoplastic polyester in the usual way in quantities of from 0.05% by weight to 3% by weight and preferably in quantities of from 0.1% by weight to 1% by weight, based on the thermoplastic, either during or after the production of the thermoplastic, the mixture obtained is subsequently homogenized at temperatures of 220° C. to 420° C. and then granulated, standard additives selected from the group consisting of impact modifiers, stabilizers, flameproofing agents, pigments, fillers and reinforcing materials optionally being incorporated in known manner in the thermoplastic polycarbonates and/or the thermoplastic polyestercarbonates and/or the thermoplastic polyesters in the usual quantities before, during or after incorporation of the mold release agents according to the invention.

The incorporation of the mold release agents according to the invention and, optionally, the standard additives mentioned in accordance with the invention may also be varied by immediately processing the thermoplastics after incorporation to the desired moldings or to other semi-finished products than granulate or to finished articles rather than regranulating them.

As already mentioned, the mold release agents according to the invention and, optionally, the standard additives mentioned may even be added to the thermoplastic polycarbonates and/or to the thermoplastic polyestercarbonates and/or to the thermoplastic polyesters during their production, for example to the organic solutions accumulating during production of the thermoplastics before they are concentrated by evaporation. Subsequent concentration by evaporation and processing to granulate or moldings may then be carried out in the usual way.

Examples of standard additives are phosphite stabilizers, epoxides against hydrolysis, antioxidants, agents for imparting solvent resistance, UV stabilizers, drip inhibitors for improving flame resistance, inert fillers and active fillers and also active pigments which may all be modified in their activity in known manner before incorporation.

The addition of the mold release agents to be used in accordance with the invention to aromatic polycarbonates or polyestercarbonates does not adversely affect their transparency or their color or cause any molecular weight degradation under thermal stressing. Aromatic polyesters do not show any negative effects either.

The use in accordance with the invention of the mold release agents according to the invention reduces demolding pressure in injection molding and enables fault-free articles of high surface quality to be obtained.

Accordingly, the present invention also relates to the processing of the molding compounds according to the invention by injection molding.

The molding compounds according to the invention may be used as moldings or injection-molded articles anywhere where the molds used require a molding compound containing mold release agents and where the moldings have to satisfy stringent demands in regard to their long-term thermal stability.

In the following Examples, all percentages relating to the additives are percentages by weight, based on the thermoplastic resin.

COMPARISON EXAMPLE 1 (without catalyst)

100 g stearyl isocyanate were stirred under nitrogen at 200° C. After 13 hours, no reduction was observed in the isocyanate value. NCO value: 14.4%.

EXAMPLE 1

100 g stearyl isocyanate and 5 g triphenyl phosphane were stirred under nitrogen for 35 hours at 200° C. NCO value: 0%.

COMPARISON EXAMPLE 2 (standard catalyst)

100 g stearyl isocyanate and 2 g dibutyltin oxide were reacted under nitrogen at 200° C. to an NCO value of 0%.

EXAMPLE 2

General procedure for the production of the polycarbonate used

Approximately 454 parts 4,4'-dihydroxydiphenyl-2,2-propane and 9.5 parts p-tert.-butylphenol are suspended in 1.5 l water. In a three-necked flask equipped with a stirrer and gas inlet pipe, the oxygen is removed from the reaction mixture by passing nitrogen through the reaction mixture while stirring for 15 minutes. 355 Parts 45% sodium hydroxide and 1000 parts methylene chloride are then added. The mixture is cooled to 25° C. While this temperature is maintained by cooling, 237 parts phosgene are added over a period of 120 minutes. An additional quantity of 75 parts of a 45% sodium hydroxide is added after 15 to 30 minutes or after uptake of the phosgene has started. 1.6 Parts triethylamine are added to the solution formed and the mixture is stirred for another 15 minutes. A highly viscous solution is obtained, its viscosity being regulated by addition of methylene chloride. The aqueous phase is separated off. The organic phase is washed with water until free from salt and alkali. The polycarbonate is isolated from the washed solution and dried. The polycarbonate has a relative viscosity of 1.29 to 1.30, as measured on a 0.5% solution in methylene chloride at 20° C. This corresponds approximately to a molecular weight of 32,000.

The polycarbonate thus obtained is extruded and granulated.

EXAMPLE 3

The quantity of mold release agent shown in Table 1 is rolled onto the polycarbonate granulate produced in accordance with Example 2 in a drum at room temperature, followed by extrusion to a strand at 280° C. The strand obtained is then granulated.

TABLE 1

| Example | Parts polycarbonate of Example 2 | Parts mold release agent |
|---------|----------------------------------|--------------------------|
| 3a**    | 100                              | 0                        |
| 3b**    | 99.5                             | 0.5 (pentaerythritol tetrastearate)* |
| 3c**    | 99.5                             | 0.5 (Comparison Example 2) |
| 3d      | 99.5                             | 0.5 (Example 1)          |

*The fatty acid ester used is Loxiol VPG 861 ®, a product of Henkel KGaA
**Examples 3a, 3b and 3c are Comparison Examples Demolding effect The effectiveness of the mold release agents used in accordance with the invention is measured on the basis of the demolding release forces required for the demolding of injection molding compounds. In this Example, the demolding forces are measured by following the pressure building up during demolding in the oil cylinder of the hydraulic ejector by means of an electric recording system throughout the entire demolding of the injection molded article in the form of a 35 mm long cylinder with a diameter of 40 mm and a wall thickness of 2 mm. Table 2 show the average demolding force required as a function of time for Examples 3a to d and for different mold temperatures:

TABLE 2

| Example | Mold temperature | Average demolding force as a function of time* |
|---------|------------------|-----------------------------------------------|
| 3a      | 90° C.           | 140 bar                                       |
|         | 110° C.          | 82 bar                                        |
|         | 130° C.          | 50 bar                                        |
| 3b      | 90° C.           | 93 bar                                        |
|         | 110° C.          | 48 bar                                        |
|         | 130° C.          | 12 bar                                        |
| 3c      | 90° C.           | 49 bar                                        |
|         | 110° C.          | 24 bar                                        |
|         | 130° C.          | 10 bar                                        |
| 3d      | 90° C.           | 47 bar                                        |
|         | 110° C.          | 24 bar                                        |
|         | 130° C.          | 8 bar                                         |

*Integration of a demolding force/time curve divided by the demolding time

Ageing Behavior

Ageing behavior under thermal stressing was determined on the basis of the reduction in molecular weight. To this end, granulates were stored in a recirculating air oven at 155° C. after incorporation of the mold release agents to be used in accordance with the invention and after regranulation (Example 3a) of the aromatic polycarbonate and the reduction in molecular weight followed on the basis of the relative solution viscosity (5 g granulate dissolved in 1 methylene chloride, as measured at 25° C., DIN 51 562 P1.3).

TABLE 3

|  | Example | | | |
|---|---|---|---|---|
|  | 3a | 3b | 3c | 3d |
| Initial value | 1.298 | 1.296 | 1.280 | 1.293 |
| Value after 500 hours | 1.292 | 1.233 | 1.184 | 1.283 |

TABLE 3-continued

| | Example | | | |
|---|---|---|---|---|
| | 3a | 3b | 3c | 3d |
| Value after 1000 hours | 1.285 | 1.208 | — | 1.258 |

Transparency and Color

Injection-molded articles produced at processing temperature of 300° C. were evaluated for transparency and color on the basis of their transmission and yellowness index. The results are shown in Table 4.

TABLE 4

| Example | Transmission* | Yellowness index* |
|---|---|---|
| 3a | 87.00% | 5.9 |
| 3b | 88.37% | 4.2 |
| 3c | 84.57% | 16.3 |
| 3d | 87.34% | 6.2 |

*As measured on 4 mm thick test plates in accordance with DIN 5033 (monochromatic specimen illumination; measuring geometry O/d; Diano spectral photometer).

We claim:

1. A process for the production of a compound containing an isocyanurate group which comprises trimerizing an aliphatic or cycloaliphatic monoisocyanate at a temperature of 50° to 250° C. and a pressure of 0.1 to 100 bar in the presence of 0.1 to 10% by weight, based on the weight of said monoisocyanate, of a triaryl phosphane catalyst and terminating the reaction when the isocyanate content is substantially 0% by weight.

2. A composition comprising
   i) 35 to 99.9% by weight of an isocyanurate group-containing compound prepared from an aliphatic or cycloaliphatic monoisocyanate and
   ii) 0.1 to 65% by weight of a triaryl phosphane, the percentages of i) and ii) being based on the total weight of components i) and ii).

3. The composition of claim 2 wherein component ii) is present in an amount of 0.1 to 10% by weight, based on the weight of component i).

4. The composition of claim 3 wherein said composition is prepared by a process which comprises trimerizing an aliphatic or cycloaliphatic monoisocyanate at a temperature of 50° to 250° C. and a pressure of 0.1 to 100 bar in the presence of 0.1 to 10% by weight, based on the weight of said monoisocyanate, of a triaryl phosphane catalyst and terminating the reaction when the isocyanate content is substantially 0% by weight.

5. A composition comprising
   a) a member selected from the group consisting of thermoplastic aromatic polycarbonates, thermoplastic aromatic polyestercarbonates, thermoplastic aromatic polyesters and mixtures thereof and
   b) 0.5 to 3.0% by weight, based on the weight of component a), of a mixture of
      i) 35 to 99.9% by weight of an isocyanurate group-containing compound prepared from an aliphatic or cycloaliphatic monoisocyanate and
      ii) 0.1 to 65% by weight of a triaryl phosphane, the percentages of i) and ii) being based on the total weight of components i) and ii).

6. The composition of claim 5 wherein component ii) is present in an amount of 0.1 to 10% by weight, based on the weight of component i).

7. The composition of claim 6 wherein component b) is prepared by a process which comprises trimerizing an aliphatic or cycloaliphatic monoisocyanate at a temperature of 50° to 250° C. and a pressure of 0.1 to 100 bar in the presence of 0.1 to 10% by weight, based on the weight of said monoisocyanate, of a triaryl phosphane catalyst and terminating the reaction when the isocyanate content is substantially 0% by weight.

8. The composition of claim 5 wherein component b) is present in an amount of 0.1 to 1.0% by weight, based on the weight of component a).

9. The composition of claim 6 wherein component b) is present in an amount of 0.1 to 1.0% by weight, based on the weight of component a).

10. The composition of claim 7 wherein component b) is present in an amount of 0.1 to 1.0% by weight, based on the weight of component a).

* * * * *